United States Patent [19]

Sears

[11] 4,190,628
[45] Feb. 26, 1980

[54] KIT FOR DETERMINING THE LEVEL OF LDL CHOLESTEROL IN BODY FLUIDS

[75] Inventor: Barry D. Sears, Marblehead, Mass.

[73] Assignee: Trustees of Boston University, Boston, Mass.

[21] Appl. No.: 955,279

[22] Filed: Oct. 26, 1978

Related U.S. Application Data

[63] Continuation-in-part of Ser. No. 853,598, Nov. 21, 1977, Pat. No. 4,126,416.

[51] Int. Cl.² .................. G01N 33/16; G01N 31/02
[52] U.S. Cl. ........................................ 422/61; 206/569
[58] Field of Search .................. 23/230 B; 260/112 R, 260/112 B, 123.5; 422/61; 206/524.1, 569

[56] References Cited
PUBLICATIONS

J. A. K. Harmony et al., J. Biol. Chem., 250 (22), 8614–8617 (1975).

*Primary Examiner*—Sidney Marantz
*Attorney, Agent, or Firm*—David E. Brook

[57] ABSTRACT

A kit for determining the level of LDL cholesterol in body fluids is disclosed which contains a plant lectin which is a specific agglutinating agent for LDL.

6 Claims, No Drawings

KIT FOR DETERMINING THE LEVEL OF LDL CHOLESTEROL IN BODY FLUIDS

GOVERNMENT SPONSORSHIP

Work relating to this invention was partially supported by Grant No. HL 1863-09 from the National Institutes of Health.

RELATED APPLICATIONS

This application is a continuation-in-part of Ser. No. 853,598, filed Nov. 21, 1977 now U.S. Pat. No. 4,126,416.

BACKGROUND OF THE INVENTION

1. Field of the Invention

This invention is in the field of clinical assay techniques.

2. Description of the Prior Art

Lipoproteins are complex particles consisting of protein and lipid which are found in the circulatory system. One of their functions is to carry water insoluble substances, such as cholesterol and cholesterol esters, for eventual cellular utilization. While all cells require cholesterol for growth, excess accumulation of cholesterol by cells is known to lead to certain diseases including atherosclerosis.

It is known that the amount of total serum cholesterol can be correlated with the incidence of atherosclerosis. However, there are a variety of classes of lipoproteins in serum which can be classified by their density. These classes include very low density lipoproteins (VLDL), low density lipoproteins (LDL), and high density lipoproteins (HDL). All of these lipoprotein classes contain varying amounts of cholesterol, and a total serum cholesterol determination is a complex average of the amount that each lipoprotein class contributes to the total lipoprotein population of the serum.

It has long been suspected that specific lipoprotein classes were more closely associated with the progression of heart disease, including atherosclerosis. In fact, more recent studies have implicated LDL as the class of lipoproteins responsible for the accumulation of cholesterol in cells whereas HDL has been shown to be important in the removal of excess cholesterol from cells. Additionally, the correlation of atherosclerosis and the levels of LDL cholesterol is much higher than a similar correlation between atherosclerosis and total serum cholesterol levels. Conversely, there seems to be a negative correlation of atherosclerosis and HDL cholesterol levels. See, Gofman, J. W., Jones, H. B., Lindgren, F. T., Lyon, T. P., Elliot, H. A., and Strisower, B., "Blood Lipids and Human Atherosclerosis," *Circulation*, 2:161–178 (1950); Barr, D. P., Russ, E. M., and Eder, H. A., "Protein-Lipid Relationships in Human Plasma, II, In Atherosclerosis and Related Conditions," *Am. J. Med.* 11:480–493 (1951); Nikkila, E., "Studies on Lipid Protein Relationships in Normal and Pathological Sera and Effect of Heparin on Serum Lipoproteins," *Scand. J. Clin. Lab. Invest. Supplement,* 5;1–101 (1952); Jencks, W. P., Hyatt, M. R.; Jetton, M. R., Mattingly, T. W., and Durrum, E. L., "A Study of Serum Lipoproteins in Normal and Atherosclerotic Patients by Paper Electrophoretic Techniques," *J. Clin. Invest.,* 35;980–990 (1956), and Miller G. J. and Miller, N. E., "Plasma-High-Density Lipoprotein Concentration and Development of Ischemic Heart Disease (technical note)," *Lancet,* 1, (7897)16–19 (1975).

Despite the desirability of determining LDL cholesterol levels from other lipoprotein cholesterol levels, a technique suitable for use in clinical laboratories has not heretofore existed. The method most often used relies upon the interaction of heparin in the presence of calcium to precipitate both LDL and VLDL. See Burstein, M. and Scholanick, H. R., *Adv. Lipid Res.,* 11, 67 (1973). To separate the LDL and VLDL fractions, ultracentrifugation techniques, which are time consuming and expensive, have to be employed.

Thus, a long existing need has existed for a simple, inexpensive, quantitative methodology to determine LDL cholesterol levels in blood plasma or other body fluids so that patients can be given a better assessment of their potential cardiovascular risk than that provided by presently used total serum cholesterol level assays.

DESCRIPTION OF THE INVENTION

This invention relates to the discovery that certain plant lectins act as specific agglutinating agents for LDL contained within body fluids such as blood plasma, blood serum, lymphatic fluid, etc. Because of this, LDL can be isolated from other lipoproteins, such as HDL, and VLDL, by agglutinating the LDL with a lectin. Thereafter, the cholesterol content of isolated LDL can be determined.

Agglutination is a clumping together of LDL particles which causes them to precipitate. While not wishing to be bound by this theory, it is believed that suitable lectins react with sugar residues of the glycolipids contained in the outer surface of LDL but not the other glycoproteins. This apparently results in a type of cross-linking which causes the agglutination and precipitation.

While most of the work described herein has been done with lectin isolated from castor beans (*Ricinus Communis*), it is believed that many other plant lectins could also be used. Since lectins are ubiquitous plant proteins, there is a wide variety from which to choose. Those lectins which are specific for galactose residues are preferred. In addition to castor bean lectin, peanut lectin is known to be specific for galactose residues. Those skilled in the art will know, or be able to ascertain using no more than routine experimentation, other lectins which selectively agglutinate LDL, especially those specific for galactose residues.

On the other hand, all lectins are not satisfactory. For example, wheat germ lectin has been found ineffective in causing selective agglutination of LDL. Other lectins, such as concanavalin A, when linked to a Sepharose 4B column, do retard the migration of LDL but also retard migration of VLDL. See McConathy, W. J. and Alaupovic, P., *FEBS Letters,* 41, 174(1974). This is believed to occur because concanavalin A interacts with mannose residues of the glycoproteins.

It has been found that LDL can be selectively precipitated from blood serum at 25° C. by castor bean lectin. At lower temperatures, such as 4° C., some VLDL is also precipitated. Thus, the agglutination reaction should be carried out at a temperature sufficient to provide selective agglutination and precipitation of LDL.

The agglutination reaction can be carried out by adding a standard solution of lectin to blood serum at a sufficient temperature. The amount of time required for the reaction depends upon the concentration of the lectin, amount of LDL present, and other such factors. In practice, the time course of agglutination of LDL by a particular lectin at a particular temperature can be plotted at varying concentrations of the lectin to provide an indication of the time required for the reaction to go to completion. Measuring the amount of agglutination can be easily done by optical methods, such as by measuring the absorbance of light at 450 nonometers.

After agglutination has occurred, the resulting agglutinated precipitate can be separated from the blood plasma by centrifugation at low speeds for short periods of time, such as 2 minutes. The precipitates can be resolubilized, if desired, by relieving the agglutination. This may be done, for example, by adding a sugar such as galactose or lactose, that competes with the sugar residues of LDL for the lectin. The resolubilized cholesterol content of the LDL can then be easily determined by known techniques, including optical techniques.

One skilled in the art will recognize that the LDL cholesterol content of the body fluid may be determined directly by analyzing the precipitate formed upon the agglutination of LDL with lectin or indirectly by analyzing the supernatant for HDL cholesterol and VLDL cholesterol following centrifugation. In the indirect method of determining LDL cholesterol, the cholesterol remaining in the supernatant following agglutination (HDL+VLDL) is substracted from the total cholesterol (HDL+LDL+VLDL) present in the body fluid. If necessary or desirable, corrections can be made for cholesterol bound to other species, such as that bound to chylomicrons.

A particularly convenient procedure for carrying out the method described herein is by means of a kit intended for the determination of LDL cholesterol in a body fluid, such as plasma or serum. Such a kit would include a reagent containing a plant lectin which was a specific agglutinating agent for LDL. The lectin reagent might also contain a stabilizer and/or preservative for lectin, such as glycerol or proteins such as bovine serum albumin. In a preferred embodiment, this plant lectin reagent would be lyophilized and a reconstituting reagent containing an aqueous base or a water-miscible solvent would also be included in the kit. The reagents may optionally also contain buffers for maintaining the reconstituted reagent system at a controlled pH and preservatives and/or stabilizers intended to prevent deterioration of the material prior to use. Although buffers are not considered a critical component of the kit reagents, most preferably a pH of about 5.4 to 8.7 would be used in carrying out the present method. Although the reconstituting reagent preferably would contain water as a solvent, a water-miscible solvent may partly or wholly be used to replace the water. Water-miscible solvents are well known to those skilled in the art and include, but are not limited to, glycerine, alcohols, glycols, or glycol ethers.

In addition to the reagent containing lectin, the kit might optionally contain an additional reagent for use in the measurement of cholesterol. Such reagents are well known to those skilled in the art. Such cholesterol determining reagents may contain sulfuric acid in combination with other chemicals such as ferric chloride or ferric perchlorate. Alternately, completely enzymatic reagents for the determination of cholesterol are available. A cholesterol determining reagent based on either the chemical or enzymatic procedure would be satisfactory for use in the present kit. Where it is desirable to measure the LDL cholesterol directly the kit may also contain a resolubilizing reagent comprising lactose in an aqueous solvent.

This invention can be further illustrated by the following specific example.

EXAMPLE 1

*Ricinus Communis* beans were obtained from Stokes Seeds, Buffalo, N.Y. The *Ricinus Communis* lectin (RCA) was isolated from the beans according to the method of Nicolson and Blaustein as modified by Podder et al. See, G. L. Nicolson and J. Blaustein. Biochem. *Biophys. Acta,* 266, 543 (1972); and S. K. Podder, A. Surolia, and B. K. Bockhawat. *Eur. J. Biochem.,* 44 151 (1974).

Plasma lipoproteins were obtained by preparative ultracentrifugation from plasma of normal male blood donors. See, R. T. Hatch and R. S. Lees, *Adv. Lipid Res.,* 6, 2 (1968). LDL was collected between 1.025 and 1.050 g/ml and washed at 1.050 g/ml; HDL was collected between densities of 1.063 and 1.21 g/ml; and VLDL was collected between densities of 1.006 and 1.019. The purity of the different lipoprotein fractions was checked by agarose gel electrophoresis.

Protein content was estimated by the method of Lowry et al. using crystalline bovine serum albumin (Sigma) as standard. See, O. H. Lowry, N. J. Rosenbrough, A. L. Farr, and R. J. Fandall, *J. Biol. Chem.,* 193, 265 (1951). Total cholesterol was estimated using ferric acetate-uranium acetate and sulphuric acid-ferrous sulphate reagents. See, A. C. Parekh and D. H. Jung, *Anal. Chem.,* 42, 1423 (1970).

The time course for the development of the agglutination of isolated LDL was followed by the increase in the turbidity of a solution using 450 nanometer light. At 25° C., the agglutination reaction reached equilibrium within 30 minutes. The agglutinated LDL was then removed by low speed centrifugation. The equilibrium levels of turbidity could be related to the actual amount of LDL in the agglutinated complex. A plot illustrating the relation between turbidity at 450 nm and the amount of LDL cholesterol that was not pelleted by low speed centrifugation was made. This cholesterol represented the percentage of LDL not agglutinated. At saturating levels of RCA, greater than 95% of thE LDL cholesterol was agglutinated and removed by low speed centrifugation. When other serum lipoproteins (HDL and VLDL) were treated with the lectin, no agglutination occurred at 25° C.; however, with VLDL some agglutination occurred at 4° C.

The agglutination of LDL was relieved by adding a solution of 4 mM lactose. This reversed the agglutination and the LDL became soluble so that the LDL cholesterol level could be determined by standard techniques. See, A. C. Parekh and D. H. Jung, *Anal. Chem.,* 42, 1423 (1970).

When a soluble mixture was placed on a gel electrophoresis slab, only a single component was observed with a mobility equal to that of LDL.

However, when the agglutination reaction was carried out at 4° C., some VLDL, in addition to LDL, was observed by gel electrophoresis.

Those skilled in the art will recognize many equivalents to the specific steps, materials, techniques, etc. described herein. Such equivalents are intended to be included within the following appended claims.

What is claimed is:

1. A diagnostic kit for detecting LDL cholesterol in a body fluid containing LDL cholesterol and another form of cholesterol selected from VLDL cholesterol, HDL cholesterol, and combinations thereof comprising, in combination:
   a. a reagent containing a lectin which is a specific agglutinating agent for LDL whereby LDL contained in said body fluid can be selectively agglutinated; and,
   b. a reagent for determining the amount of cholesterol in said specifically agglutinated LDL.

2. A diagnostic kit of claim 1 wherein said reagent containing a lectin has been lyophilized.

3. A diagnostic kit of claim 2 additionally containing a reconstituting reagent for said lyophilized lectin reagent, said reconstituting reagent containing an aqueous-based or water-misicible solvent.

4. A diagnostic kit of claim 3 additionally including a resolubilizing reagent for said specifically agglutinated LDL.

5. A diagnostic kit of claim 4 wherein said resolubilizing reagent comprises lactose in an aqueous solvent.

6. In a diagnostic kit for determining LDL cholesterol in a body fluid containing LDL cholesterol and another form of cholesterol, the improvement of including in said diagnostic kit a reagent containing a lectin which is a specific agglutinating agent for LDL.

* * * * *